United States Patent [19]

Lauermann et al.

[11] Patent Number: 4,466,959
[45] Date of Patent: Aug. 21, 1984

[54] PREPARATION FOR UDDER CARE AND DISINFECTION FOR DAIRY ANIMALS

[75] Inventors: Georg Lauermann, Metzkausen; Siegfried Scholz, Düsseldorf; Ferdinand Koch, Hilden, all of Fed. Rep. of Germany

[73] Assignee: Henkel Kommanditgesellschaft auf Aktien, Düsseldorf-Holthausen, Fed. Rep. of Germany

[21] Appl. No.: 409,780

[22] Filed: Aug. 20, 1982

[30] Foreign Application Priority Data

Mar. 15, 1982 [DE] Fed. Rep. of Germany ....... 3209328

[51] Int. Cl.$^3$ ..................... A61K 33/18; A61K 47/00
[52] U.S. Cl. ..................................... 424/150; 424/358
[58] Field of Search .......................................... 424/150

[56] References Cited

U.S. PATENT DOCUMENTS

| | | |
|---|---|---|
| 3,663,694 | 5/1972 | Hall . |
| 3,728,449 | 4/1973 | Cantor et al. .................. 424/150 |
| 3,914,411 | 10/1975 | Askienazy et al. .................. 424/150 |
| 3,950,554 | 4/1976 | Prince .................. 424/150 |
| 4,012,504 | 3/1977 | Eckols .................. 424/150 |
| 4,130,640 | 12/1978 | Chazan et al. .................. 424/150 |
| 4,288,428 | 9/1981 | Föll et al. . |

FOREIGN PATENT DOCUMENTS

17639 10/1980 European Pat. Off. .
2105151 4/1972 France .

*Primary Examiner*—Sam Rosen
*Attorney, Agent, or Firm*—Hammond & Littell, Weissenberger & Dippert

[57] ABSTRACT

This invention is directed to a preparation useful on dairy animals. More specifically, this invention is directed to a preparation for the disinfection of teats and the care of udders of dairy animals which comprises:

(a) from about 84.4 to 91.6 percent by weight, based upon the weight of the total preparation, of deionized water;
(b) from about 3 to 5 percent by weight, based upon the weight of the total preparation, of glycerin;
(c) from about 3 to 5 percent by weight, based upon the weight of the total preparation, of paraffin oil;
(d) from about 1 to 2.5 percent by weight, based upon the weight of the total preparation, of saturated $C_{16}$–$C_{18}$-fatty alcohols;
(e) from about 0.4 to 0.6 percent by weight, based upon the weight of the total preparation, of an iodine complex with disinfecting action, wherein the content of active iodine is from about 800 to 1200 ppm and the viscosity is from about 25 to 35 sec. as measured at 20° C. in a Ford beaker with a 4 mm nozzle.

3 Claims, No Drawings

PREPARATION FOR UDDER CARE AND DISINFECTION FOR DAIRY ANIMALS

FIELD OF THE INVENTION

This invention is directed to a preparation useful on dairy animals. More specifically, this invention is directed to a preparation useful for the disinfection of teats and in the care of udders of dairy animals.

BACKGROUND OF THE INVENTION

Infectious inflammations of the udder (cattle mastitis), which especially affect highly productive cattle, are the cause of considerable losses of milk. In addition, such inflammations frequently result in the premature slaughter of the animals if the mastitis becomes chronic with consequent limitation to three or even two productive teats (failing of individual udder quarters).

The recommended prophylaxis against infection is the dipping of the teats into an effective disinfecting solution after milking, which reduces the number of soil and disease organisms adhering to the skin of the teat, especially in the area of the teat openings. This method includes low-viscosity aqueous solutions that contain a relatively high concentration of active disinfectants to guarantee an adequate effectiveness. Since these substances are also skin irritants of varying intensity, the preparations usually contain skin-protecting substances. Preparations of this type are described, for example, in U.S. Pat. No. 3,993,777 and *Deutsche Tierarztliche Wochenschrift*, Vol. 86 (1979), pages 85–88.

However, the above-mentioned teat dipping preparations are unsuited for the care of the udder since, in contrast to the teat skin, the udder skin is extremely sensitive to disinfectants and skin irritations are a common occurrence. For this reason, special milking fats and emulsions are available for udder care, which keep the skin of the udder supple and reduce the loss of moisture. Rough and cracked udder skin can also be treated with these to provide pain relief. These preparations are, however, unsuited for the prophylaxis of mastitis as they lack an adequate disinfectant action.

OBJECTS OF THE INVENTION

It is an object of the invention to provide a novel preparation useful in the care of dairy animals.

It is also an object of the invention to provide a preparation useful for the disinfection of teats and in the care of udders of dairy animals.

It is a further object of the invention to provide a preparation for the disinfection of teats and the care of udders in dairy animals which preparation is based upon iodine-containing disinfectants and skin-protecting substances and which comprises an aqueous emulsion with an elevated viscosity.

It is a yet further object of the invention to provide a preparation for the disinfection of teats and the care of udders of dairy animals which comprises:

(a) from about 84.4 to 91.6 percent by weight, based upon the weight of the total preparation, of deionized water;
(b) from about 3 to 5 percent by weight, based upon the weight of the total preparation, of glycerin;
(c) from about 3 to 5 percent by weight, based upon the weight of the total preparation, of paraffin oil;
(d) from about 1 to 2.5 percent by weight, based upon the weight of the total preparation, of saturated $C_{16}$–$C_{18}$-fatty alcohols;
(e) from about 1 to 2.5 percent by weight, based upon the weight of the total preparation, of nonionic emulsifying agent; and
(f) from about 0.4 to 0.6 percent by weight, based upon the weight of the total preparation, of an iodine complex with disinfecting action, wherein the content of active iodine is from about 800 to 1200 ppm and the viscosity is from about 25 to 35 sec. as measured at 20° C. in a Ford beaker with a 4 mm nozzle.

These and other objects of the invention will become more apparent in the discussion below.

DETAILED DESCRIPTION OF THE INVENTION

The purpose of the invention is the creation of a preparation that is suitable as a dipping preparation for the disinfecting of teats after milking and at the same time is also suitable for the care of the sensitive skin of the udder and consequently eliminates the application of two separate preparations. This purpose is achieved by providing a liquid preparation with elevated viscosity and a disinfectant content that is adjusted so that the dipping procedure applies an adequate amount of disinfectant to the teat while preventing skin irritations at the udder. Thus the subject of the invention is a preparation for teat disinfection and udder care of dairy animals, especially cattle, based upon iodine-containing disinfectants and skin-protecting substances, characterized by the fact that the preparation is an aqueous emulsion of elevated viscosity and has the following composition:

(a) from about 84.4 to 91.6 percent by weight, based upon the weight of the total preparation, of deionized water;
(b) from about 3 to 5 percent by weight, based upon the weight of the total preparation, of glycerin;
(c) from about 3 to 5 percent by weight, based upon the weight of the total preparation of paraffin oil;
(d) from about 1 to 2.5 percent by weight, based upon the weight of the total preparation, of saturated $C_{16}$–$C_{18}$-fatty alcohols;
(e) from about 1 to 2.5 percent by weight, based upon the weight of the total preparation, of nonionic emulsifying agent; and
(f) from about 0.4 to 0.6 percent by weight, based upon the weight of the total preparation, of an iodine complex with disinfecting action, the active iodine content being from about 800 to 1200 ppm. The viscosity of the preparation is from about 25 to 35 sec. as measured at 20° C. in a Ford beaker with a 4 mm nozzle.

The preparation is an aqueous emulsion with a viscosity defined within narrow limits and an adjusted content of an iodine complex with disinfectant action. The increased viscosity permits the adherence to the teat of an amount of liquid adequate for the disinfecting effect and for the reliable closing of the teat canal by dipping of the teats. This process prevents with certainty the development of mastitis. Skin irritations due to application to the udder are avoided with the low disinfectant content. The skin-protecting effect of the preparation becomes active at the teat as well as at the udder. Problems with residues, which may occur with the application of more concentrated preparations, are largely avoided.

The pH of the preparation is adjusted to that of the healthy skin, that is, to a pH of from about 2.5 to 3.5, preferably about 3. The viscosity corresponds to a running time of from about 25 to 35 seconds as measured at 20° C. in a Ford beaker with a 4 mm nozzle orifice.

The components of the preparation have the following function:

deionized water (condensed water) is the solvent and diluent;

glycerin (pharmaceutical grade, DAB 7) serves as moisturizer for the skin; and liquid paraffin (pharmaceutical grade, DAB 8) keeps the skin supple.

The saturated $C_{16}-C_{18}$-fatty alcohols, particularly in the form of a mixture of equal parts of the alcohols, also provide suppleness and smoothness. In dispersed form, they lend the preparation the character of a lotion and consequently are also used to adjust the viscosity.

The nonionic emulsifying agent, mainly polyglycol ethers of fatty alcohols of alkylphenols, is used to prepare a stable dispersion of liquid paraffin and fatty alcohol. Use of emulsifying agents comprising colloidally dispersed mixtures of saturated $C_{16}-C_{18}$-fatty alcohols and saturated $C_{16}C_{18}$-fatty alcohol polyglycol ethers with from 10 to 25 ethylene oxide units at a ratio of 1:0.15 to 0.5 is preferred over the separate use of fatty alcohols and polyglycol ether.

Useful iodine complexes with disinfecting action comprise adducts of iodine with polyglycol ethers, for example, alkylphenol polyglycol ethers or polyethylene oxide/polypropylene oxide block polymers, or with polyvinylpyrrolidene. This type of product is commercially available under the name iodophor. A known product of this type is ANTAROX®VRO-20, which is available from GAF, Federal Republic of Germany. The product according to the invention contains from about 0.4 to 0.6 percent by weight of iodine complex, corresponding to from about 800 to 1200 ppm of active iodine.

The preparation is applied in the usual way as a teat dipping agent in the morning and evening after milking, as well as once each day for dry cows until they have given birth to a calf, and as skin-care agent for the entire udder area, as needed. Preferably the teats and udder are dipped into the solution, rather than just the teats, as with previous teat dipping agents. Other possible applications are the udder care of small ruminants, as well as the care of the dugs of farrow sows. A reduction of organisms over the entire udder is achieved, and consequently the rate of reinfection is lowered. At the same time the skin receives optimal care, it remains supple and resistant to environmental influences. The preparation thus is suitable not only for regular prophylactic use on healthy dairy animal herds but especially also for herds with mastitis problems and for the sanitation of herds to prevent mastitis.

An additional advantage over conventional milking salves and lotions is the low danger of spreading the organisms during use, due to the disinfectant content.

The following example is intended to illustrate the invention and should not be construed as limiting the invention thereto.

EXAMPLE

A preparation suitable as teat dipping agent as well as for the care of udders for dairy cows had the following composition:

| Component | Percent by Weight |
|---|---|
| Deionized water | 91.4 |
| Glycerin, DAB 7 | 3.0 |
| Liquid paraffin (viscous), DAB 8 | 3.0 |
| Colloidally dispersed mixture of (a) $C_{16}-C_{18}$-fatty alcohols and (b) adduct of $C_{16}-C_{18}$-fatty alcohols + 20 EO ((a):(b) weight ratio of 1:0.2) | 2.0 |
| 36% Iodine complex (ANTAROX VRO-20) | 0.6 |
| | 100.0 |

The agent, which contained 1200 ppm active iodine, was well tolerated on the teats and the udder, even during long-term application.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A preparation for the disinfection of teats and the care of udders of dairy animals which comprises:
   (a) from about 84.4 to 91.6 percent by weight, based upon the weight of the total preparation, of deionized water;
   (b) from about 3 to 5 percent by weight, based upon the weight of the total preparation, of glycerin;
   (c) from about 3 to 5 percent by weight, based upon the weight of the total preparation, of paraffin oil;
   (d) from about 1 to 2.5 percent by weight, based upon the weight of the total preparation, of saturated $C_{16}-C_{18}$-fatty alcohols;
   (e) from about 1 to 2.5 percent by weight, based upon the weight of the total preparation, of nonionic emulsifying agent; and
   (f) from about 0.4 to 0.6 percent by weight, based upon the weight of the total preparation, of an iodine complex with disinfecting action,
wherein the content of active iodine is from about 800 to 1200 ppm and the viscosity is from about 25 to 35 sec. as measured at 20° C. in a Ford beaker with a 4 mm nozzle.

2. A method of disinfecting teats and/or treating the udders of dairy animals, which comprises administering an effective amount of the preparation of claim 1.

3. The method of claim 2, wherein the teats or teats and udder are dipped into a container of said preparation.

* * * * *